US00PP28113P2

(12) United States Plant Patent
Reijm

(10) Patent No.: US PP28,113 P2
(45) Date of Patent: Jun. 13, 2017

(54) ***DRACAENA* PLANT NAMED 'REIJDRAMAS2'**

(50) Latin Name: ***Dracaena fragrans* (L.)**
Varietal Denomination: REIJDRAMAS2

(71) Applicant: Kwekerij Reijm Nieuwerkerk B. V., Nieuwerkerk aan den IJssel (NL)

(72) Inventor: Jacob Reijm, Nieuwerkerk aan den IJssel (NL)

(73) Assignee: Kwekerij Reijm Nieuwerkerk B. V., Nieuwerkerk aan den IJssel (NL)

( * ) Notice: Subject to any disclaimer, the term of this patent is extended or adjusted under 35 U.S.C. 154(b) by 0 days.

(21) Appl. No.: 14/999,336

(22) Filed: Apr. 25, 2016

(51) Int. Cl.
*A01H 5/12* (2006.01)

(52) U.S. Cl.
USPC ..... Plt./383

(58) Field of Classification Search
USPC ..... Plt./383
See application file for complete search history.

*Primary Examiner* — Annette Para
(74) *Attorney, Agent, or Firm* — Samuel R. McCoy, Jr.

(57) ABSTRACT

A new and distinct *Dracaena fragrans* cultivar named 'REIJDRAMAS2' which is characterized by a globular plant shape, moderate to strong branching, near-orbicular leaves with heavily undulated margins, a unique cupped to undeeply tubular leaf aspect, a hastate to tubular leaf base, and the stability of these characteristics from generation to generation.

2 Drawing Sheets

Latin name of the genus and species: The Latin name of the genus and species of the novel variety disclosed herein is *Dracaena fragrans* (L.) Ker Gawl.

Variety denomination: The inventive variety of *Dracaena fragrans* disclosed herein has been given the variety denomination 'REIJDRAMAS2'.

BACKGROUND OF THE INVENTION

Parentage: 'REIJDRAMAS2' is the result of a spontaneous whole-plant mutation of *Dracaena fragrans* 'REIJDRAMAS' which was discovered at the inventor's commercial greenhouse in Nieuwerkerk aan den IJssel, the Netherlands in March of 2014. After identifying the new variety as a potentially interesting selection, the inventor continued confidential testing to assess the stability of the unique characteristics of this variety. 'REIJDRAMAS2' was ultimately selected for commercialization in March of 2015 due to its unique foliage variegation and plant habit.

Asexual Reproduction: Asexual reproduction was initiated in March of 2015, by way of meristematic tissue culture, in Nieuwerkerk aan den IJssel, the Netherlands. Through four subsequent generations, the unique features of this cultivar have proven to be stable and true to type.

SUMMARY OF THE INVENTION

The cultivar 'REIJDRAMAS2' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'REIJDRAMAS2'. These characteristics in combination distinguish 'REIJDRAMAS2' as a new and distinct *Dracaena fragrans* cultivar:

1. 'REIJDRAMAS2' is a large, vigorous plant; and
2. 'REIJDRAMAS2' exhibits yellow-green foliage with dark green stripes; and
3. 'REIJDRAMAS2' exhibits very glossy foliage; and
4. 'REIJDRAMAS2' exhibits improved cold hardiness.

BOTANICAL DESCRIPTION OF THE PLANT

Figure 1:
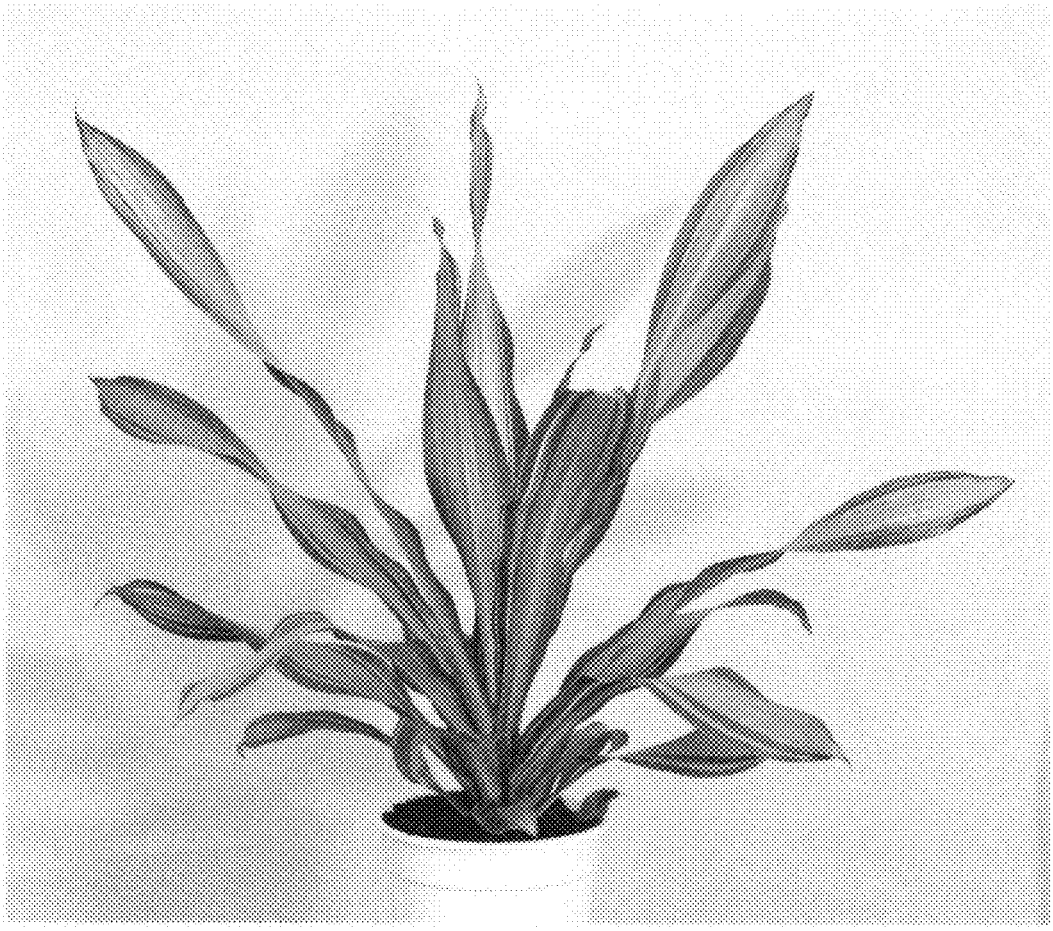
FIG. 1 illustrates, as nearly true as it is reasonably possible to make the same in color photographs of this type, an exemplary plant of 'REIJDRAMAS2' grown in a commercial greenhouse in Nieuwerkerk aan den IJssel, the Netherlands. This plant is approximately 40 week old, shown planted in a 24 cm nursery container.
Figure 2:
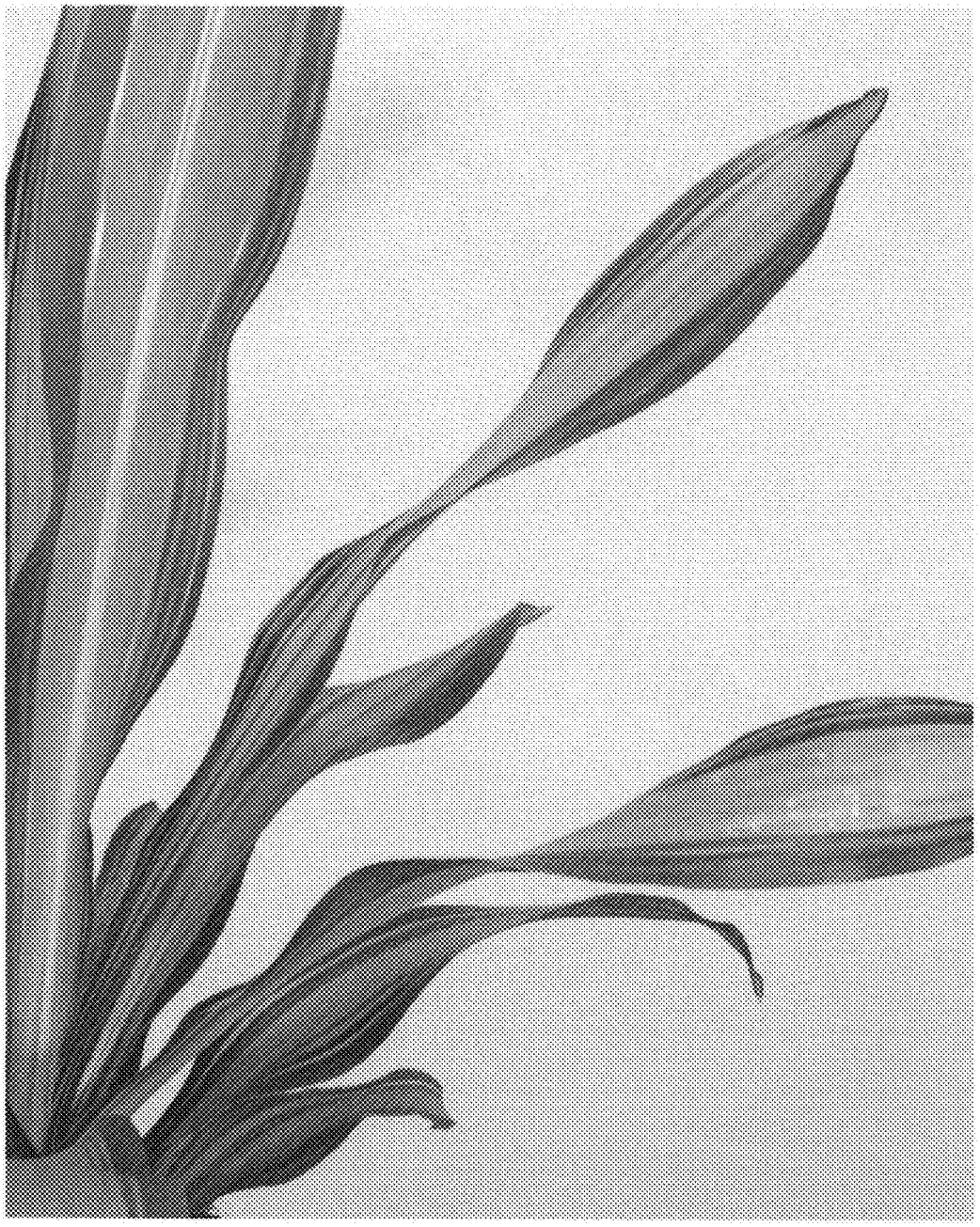
FIG. 2 illustrates, as nearly true as it is reasonably possible to make the same in color photographs of this type, the typical mature foliage habit of 'REIJDRAMAS2'.

The following observations and measurements made in March of 2016 describe averages from a sample set of six specimens of 40 week-old 'REIJDRAMAS2' plants grown in 24 cm nursery containers at commercial greenhouse in Nieuwerkerk aan den IJssel, the Netherlands. Plants were produced using conventional greenhouse production protocols which consisted of flood benches for irrigation and scheduled liquid fertilizer applications. Biological pest control measures were utilized, but no chemical pest or disease control measures were applied during production. Plants were grown under shade and no photoperiodic treatments or artificial light was given to the plants.

Those skilled in the art will appreciate that certain characteristics will vary with older or, conversely, with younger plants. 'REIJDRAMAS2' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'REIJDRAMAS2' and a comparison with the parent and closest known comparator, *Dracaena fragrans* 'REIJDRAMAS', is provided below.

Plant description:

*Growth habit*.—Perennial with a broad, oblong growth habit.

*Plant shape*.—Upright.

*Height from soil level to top of foliar plane*.—76.7 cm, on average.

*Plant diameter*.—Average of 96.1 cm.

*Growth rate*.—Moderately fast to fast.

*Plant vigor*.—Moderate to vigorous.

*Propagation*.—Type — Stem cuttings. Time to produce a rooted cutting — Approximately 16 weeks at 20 to 21 degrees Celsius. Crop time — Approximately 1 year to produce a marketable plant in a 17 cm container, and 1.5 years to produce a marketable plant in a 24 cm container. Pinching is not required to produce a well-shaped plant, but it does promote branching.

*Disease and pest resistance or susceptibility*.—Neither resistance nor susceptibility to normal diseases and pests of *Dracaena* has been observed.

*Environmental tolerances*.—Adapt to, at least, USDA Zones 10 to 13 and temperatures as high as 40 degrees Celsius; moderate tolerance to wind and rain.

Root system:

*General*.—Moderately thick, moderately fibrous, not fleshy.

*Color*.—Yellow-White, RHS 158C.

Stems:

*Branching habit*.—Not freely branching; typically there is only one main stem present and no lateral branches. Will develop lateral branches if pruned.

*Dimensions*.—10.8 cm long and 2.4 cm in diameter, on average.

*Internode length*.—0.4 cm, on average.

*Texture, pubescence and luster*.—Smooth, glabrous, and moderately glossy.

*Aspect*.—Vertical.

*Strength*.—Strong.

*Color, juvenile*.—Yellow-green, RHS 150D.

*Color, mature*.—Yellow-green, RHS 145D to 150D.

*Color at internodes*.—Yellow-green, RHS 145D to 150D.

Foliage:

*Arrangement*.—Alternate; spiraling.

*Attachment*.—Sheathing.

*Quantity*.—Approximately 23 leaves on the main stem.

*Shape*.—Lorate.

*Dimensions*.—72.9 cm long by 9.4 cm wide, on average.

*Aspect*.—Leaves are held in an average angle of 55 degrees to the stem; leaves are curved and slightly twisted, with tips pointing downward in an average angle of minus 50 degrees.

*Apex*.—Acute with a blunt tip.

*Base*.—Sheathing.

*Sheath*.—Dimensions — 5.6 cm long and 6.7 cm wide. Color, adaxial surface — Yellow-green, RHS 150D. Color, abaxial surface — Yellow-green, in between RHS 145C and 150C to 150D.

*Margin*.—Entire and coarsely undulated.

*Pubescence, texture and luster of adaxial surface*.—Glabrous, smooth, and glossy.

*Pubescence, texture and luster of abaxial surface*.—Glabrous, smooth, and slightly glossy.

*Color*.—Juvenile foliage, adaxial surface — Green, in between RHS 137C to 143A yet closest to 137C; broadly axially (lengthways) and centrally striped yellow green, in between RHS 144C and N144A. Juvenile foliage, abaxial surface — Green, RHS 137C; broadly axially (lengthways) and centrally striped yellow-green, RHS 144B, 144C and 145A. Mature foliage, adaxial surface — Green to yellow-green, in between RHS N137A and 147A yet closest to N137A; broadly axially (lengthways) and centrally striped green and yellow-green, RHS 143C, 144A, and N144A to N144C. Mature foliage, abaxial surface — Green, RHS N137A and N137B; broadly axially (lengthways) and centrally striped yellow-green, RHS 144A, 144B and 150D.

*Venation*.—Venation pattern — Parallel. Color, mature adaxial surface — Same color as the leaf surface: Green to yellow-green, in between RHS N137A and 147A yet closest to N137A; broadly axially (lengthways) and centrally striped green and yellow-green, RHS 143C, 144A, and N144A to N144C. Color, mature abaxial surface — Main vein is yellow-green, in between 150C and 151D; other veins are the same color as the leaf surface: Green, RHS N137A and N137B; broadly axially (lengthways) and centrally striped yellow-green, RHS 144A, 144B and 150D.

*Petiole*.—Not present; leaves are sheathing.

Inflorescence: No flowering has been observed to date.

COMPARISONS WITH THE PARENT PLANT AND CLOSEST KNOWN COMPARATOR

Plants of the new cultivar 'REIJDRAMAS2' differ from the parent, *Dracaena fragrans* 'REIJDRAMAS' (U.S. Plant Pat. No. 24,682), which is also the closest known comparator, in several physical characteristics which are compared in Chart 1.

CHART 1

| Characteristic | 'REIJDRAMAS2' | 'REIJDRAMAS' |
|---|---|---|
| Leaf sheath color, upper surface. | Yellow-green RHS 150D. | Yellow-green RHS 145D. |
| Leaf sheath color, lower surface. | Between Yellow-green RHS 145C and 150C to 150D on the lower surface. | Yellow-green RHS 145D. |
| Juvenile leaf color, upper surface. | Green, in between RHS 137C and 143A, yet closest to 137C; broadly axially (lengthways) striped and centered yellow-green, in between RHS 144C and N144A. | Green to yellow-green, RHS 143A to 144A and 144B; axially (lengthways) striped yellow-green; RHS 150C to 150D. |

CHART 1-continued

| Characteristic | 'REIJDRAMAS2' | 'REIJDRAMAS' |
|---|---|---|
| Juvenile leaf color, lower surface. | Green, RHS 137C, and broadly axially striped and centered yellow-green, RHS 144B, 144C and 145A. | Green, RHS 137D to 138A and 138B, and axially striped yellow-green, RHS 145A to 150C. |
| Mature leaf color, upper surface. | Green to yellow-green, in between RHS N137A and 147A yet closest to N137A; broadly axially striped and centered green and yellow-green, RHS 143C, 144A and N144A to N144C. | Green, in between RHS 141A and 143A but darker; axially striped yellow-green; RHS N144B to N144C. |

CHART 1-continued

| Characteristic | 'REIJDRAMAS2' | 'REIJDRAMAS' |
|---|---|---|
| Mature leaf color, lower surface. | Green, N137A and N137B, and broadly axially striped and centered yellow-green, RHS 144A, 144B and 150D. | Green, RHS 137D, and axially striped yellow-green, RHS N144C. |

That which is claimed is:

1. A new and distinct variety of *Dracaena fragrans* plant named 'REIJDRAMAS2', substantially as described and illustrated herein.

* * * * *